United States Patent
Maggiarosa et al.

(10) Patent No.: US 8,513,447 B1
(45) Date of Patent: Aug. 20, 2013

(54) PREPARATION OF TRI-ALKYL GALLIUM OR TRI-ALKYL INDIUM COMPOUNDS

(71) Applicants: Nicola Maggiarosa, Kamen (DE); Angelika Preetz, Werne (DE); David J. Sikora, Middlebury, CT (US)

(72) Inventors: Nicola Maggiarosa, Kamen (DE); Angelika Preetz, Werne (DE); David J. Sikora, Middlebury, CT (US)

(73) Assignee: Chemtura Corporation, Middlebury, CT (US)

( * ) Notice: Subject to any disclaimer, the term of this patent is extended or adjusted under 35 U.S.C. 154(b) by 0 days.

(21) Appl. No.: 13/744,522

(22) Filed: Jan. 18, 2013

Related U.S. Application Data

(60) Provisional application No. 61/593,502, filed on Feb. 1, 2012, provisional application No. 61/593,537, filed on Feb. 1, 2012.

(51) Int. Cl.
*C07F 1/00* (2006.01)

(52) U.S. Cl.
USPC .................................................. 556/1

(58) Field of Classification Search
USPC .................................................. 556/1
See application file for complete search history.

(56) References Cited

U.S. PATENT DOCUMENTS

| | | | |
|---|---|---|---|
| 3,318,931 A | 5/1967 | Dötzer et al. | |
| 5,455,364 A | 10/1995 | Yako et al. | |
| 5,756,786 A | 5/1998 | Power et al. | |
| 6,495,707 B1 | 12/2002 | Leese et al. | |
| 6,770,769 B2 * | 8/2004 | Shenai-Khatkhate et al. | .... 556/1 |

OTHER PUBLICATIONS

Journal of the American Chemical Society. John J. Eisch "*Organometallic Compounds of Group III. I. The Preparation of Gallium and Indium Alkyls from Organoaluminum Compounds*", vol. 84, No. 19, pp. 3605-3609 (1962).

* cited by examiner

*Primary Examiner* — Porfirio Nazario Gonzalez
(74) *Attorney, Agent, or Firm* — Joseph Suhadolnik

(57) ABSTRACT

Trialkyl metal compounds, such as trialkyl gallium and indium compounds, are prepared in high yield and high purity by the addition of a trialkyl aluminum compound to a mixture prepared by adding a metal trihalide, e.g., $GaCl_3$ or $InCl_3$, and a halide salt of a monovalent metal to an ionic liquid such as a molten salt of the formula $M[AlR_nX_{(4-n)}]$ wherein M is a monovalent metal such as Li, Na, K or Cs, R is an alkyl group X is a halide and n is a number from 1 to 3, typically at temperatures of from 75 to 160° C.

20 Claims, No Drawings

PREPARATION OF TRI-ALKYL GALLIUM OR TRI-ALKYL INDIUM COMPOUNDS

This application claims benefit under 35 USC 119(e) of U.S. provisional applications No. 61/593,502, filed Feb. 1, 2012, and 61/593,537, filed Feb. 1, 2012, the disclosures of which are incorporated herein by reference.

Trialkyl metal compounds, such as trialkyl gallium and indium compounds, are prepared in high yield and high purity by adding a trialkyl aluminum compound to a mixture formed by combining a gallium or indium trihalide with a halide salt of a monovalent metal, e.g., a halide salt of as Li, Na, K or Cs, in an ionic liquid solvent, i.e., a molten salt such as a molten mixed metal salt of aluminun, for example a salt or a mixture of salts of the formula $M[AlR_nX_{(4-n)}]$ wherein M is a monovalent metal such as Li, Na, K or Cs, R is an alkyl group X is a halide and n is a number from 1 to 3.

BACKGROUND

Many high value uses of organometallic compounds, such as the preparation of semiconductor materials in electronic and optoelectronic applications, require extremely pure organo metallic materials. Organo metallic compounds of Group III elements of the Periodic Table, particularly the lower alkyl compounds of these elements, are extensively used to deposit compounds of their constituent elements on substrates by chemical vapor deposition. For example, gallium arsenide semiconductor layers have been deposited on substrates by combining the vapors of a gallium source such as trimethylgallium with an arsenic source such as arsine at an elevated temperature in the presence of a suitable substrate. Similar processes are used to form other compounds, for example, indium phosphide from trimethylindium and phosphine.

Films of these material may be deposited on surfaces using a variety of techniques including chemical vapor deposition (CVD), physical vapor deposition (PVD), and other epitaxial techniques such as molecular beam epitaxy (MBE), liquid phase epitaxy (LPE), chemical beam epitaxy (CBE) and atomic layer deposition (ALD). CVD processes for example can be used to deposit a metal layer, either at atmospheric pressure or at reduced pressures, by decomposing volatile organometallic precursor compounds, e.g., trimethyl gallium or trimethylindium at elevated temperatures. It is generally accepted that the purity level of the precursor alkyls limits the obtainable purity of the resultant epitaxial layer, which in turn determines the technological usefulness of the resultant device.

This invention relates in particular to the preparation of organometallic compounds suitable for use in vapor deposition and epitaxial growth of metal-containing films.

A number of conceptually simple methods exist for preparing the trialkyl gallium and indium compounds used in the above film forming processes, for example, reaction of metal halides with a Grignard reagent or alkyl lithium in an ether or hydrocarbon solvent, or addition of an organo halide to a molten metal. Thus, trimethyl gallium can be prepared by the reaction of gallium trichloride with 3 equivalents of methyl Grignard or methyl lithium, and trimethyl indium has been formed by the reaction of molten indium metal and methyl chloride. Transalkylation between certain alkyl metal compounds and metal halides is also well known. For example, trimethyl indium has been formed by the reaction of indium trihalide and trimethyl aluminum.

However, there are recognized drawbacks to the existing methods especially when highly pure materials are needed. Some reactions suffer from poor conversions or the formation of products which are difficult to isolate or adequately purify. For example, reaction with a Grignard reagent typically requires a solvent such as ether which is known to tightly complex with, for example, trialkylindium compounds making separation extremely difficult. U.S. Pat. No. 5,455,364 discloses a process for purifying a trialkyl Group III metal compound formed form a Grignard reaction wherein an alkali halide, preferably potassium fluoride is added to the crude product mixture to complex oxygen compounds and distilling the desired product. Also, while many of the more useful organometallic compounds are volatile, e.g., trimethyl aluminum, gallium and indium, so are many of the solvents used in alkylation reactions making separation by distillation difficult.

Along with the issue of purification, transalkylation processes often suffer from the incomplete transfer of alkyl groups from metal alkyl compound to metal chloride. For example, U.S. Pat. No. 3,318,931 discloses a process wherein a threefold excess of trialkyl aluminum is added to gallium trichloride to form the trialkyl gallium compound. That is, only one alkyl group is efficiently transferred from the stating tri-alkyl aluminum to the gallium halide resulting in a mixture of trialkyl gallium and dialkyl aluminum chloride.

U.S. Pat. No. 5,756,786 discloses a method for producing trimethylindium by reacting indium trichloride with a large excess of trimethyl aluminum in the presence of 2 equivalents of potassium bromide in a high boiling hydrocarbon solvent.

U.S. Pat. No. 6,495,707 discloses a continuous method for producing organometallic compounds such as trimethylindium and trimethylgallium by introducing a metal precursor e.g., gallium trichloride and an alkylating agent, e.g., trimethyl aluminum, directly into a distillation apparatus, where upon reaction the volatile trimethyl gallium is distilled away from the remainder of the reaction mixture. An excess of at least 3.5:1 trimethyl aluminum to Gallium precursor must be present in the reaction zone.

Clearly, a process which would allow for the clean transfer of at least two or possibly all three alkyl groups from a trialkyl aluminum to a gallium or indium trihalide would offer a significant improvement in the preparation of these high value trialkyl metal compounds.

Many attempts have been made to improve the efficiency of the transfer of alkyl from, e.g., trimethyl aluminum to gallium trichloride. J. Am. Chem. Soc., vol 84, p 3605-3610 discloses a study of the reaction between triethyl aluminum and gallium or indium trichloride or tribromide. In one experiment, three equivalents of triethyl aluminum is reacted with gallium trichloride in a highly exothermic reaction to provide triethyl gallium in a 38% yield. The subsequent addition of potassium bromide to this initial product mixture and reheating the mixture raised the yield of triethyl gallium to 89% based on gallium. It was postulated that various salts are formed in the reaction. For example, it is believed that $Ga[AlEt_2Cl_2]_3$ is formed in the initial reaction and that the addition of KBr leads to the presence of $K[AlEt_2Cl_2]$ in the final product mixture.

While the addition of KBr to the initial reaction product mixture enhances the ultimate yield of trialkyl gallium, a large excess of trialkyl aluminum is still needed due to partial transfer of alkyl groups.

JP 2006/265168 discloses a process for forming trialkyl gallium by heating a mixture of trialkyl aluminum and gallium trihalide either in hydrocarbon solvents or neat. Although it suggests that ratios of trialkyl aluminum to gallium trihalide of 4:1 to 1:1 can be used, all reactions exemplified use about 2.5:1 or ratio of trialkyl aluminum to gallium trihalide. No evidence is provided that good yields or high purity at lower ratios could be obtained.

GB 820,146 discloses a process for forming B, Hg, Ga, Ge, As, Sb and Bi metal alkyls from the corresponding metal chlorides by reacting a mixture comprising a trialkyl aluminum, an alkali metal halide and the metal chloride. The alkali metal salt is believed to from a complex with the aluminum species. Each of the three alkyl groups of the trialkyl aluminum are transferred to the metal chloride and yields of 80 to 90% based on aluminum trihalide are reported, but no data on the conversion of $GaCl_3$ to $Ga(alkyl)_3$ is reported. The disclosure suggests that the reaction may be run in the absence of solvent, although no such reaction is exemplified.

In the production of semiconductors via, e.g., vapor deposition techniques, ultra high purity materials, i.e., materials with level of impurities of <0.1 wt %, preferably <1 ppm, or even <1 ppb are required and the presence of even minute amounts of interfering volatile contaminates is problematic. The presence of residual solvent from the preparation of a trialkyl gallium for example can cause significant difficulty.

One way to avoid contaminants from an organic solvent is to prepare the trialkyl metal compound in the absence of solvent. For example, it has been found by the present inventors that trialkyl gallium or trialkyl indium compounds can be prepared by reacting a tetrahalo gallium salt with a trialkyl aluminum in the absence of an organic solvent. For example, trialkyl gallium compounds are formed by adding a trialkyl aluminum compound to a tetrahalo gallium salt of formula $MGaX_4$ or $M(GaX_4)_2$, wherein M is a monovalent metal such as Li, Na, K or Cs or a divalent metal such as Mg or Ca, in the absence of an organic solvent, with high yield and high purity. The tetrahalo gallium salt is fomed by adding a metal halide salt, e.g., a Li, Na or K chloride or bromide, to molten $GaCl_3$. The trialkyl aluminum is added directly to this mixture at temperatures high enough to ensure mixing.

However, during the course of the reaction, efficient mixing can become problematic as various salts and high melting inorganic species are formed. This problem is expected to be more significant when preparing indium compounds as corresponding indium salts have a higher melting point and untenable temperatures may be required.

There remains a need for a highly reliable and efficient route to ultra pure metal alkyls such as trialkyl gallium.

It is believed, as seen in the above cited art, that in the reaction of, e.g., $GaCl_3$ with $Al(CH_3)_3$ to form $Ga(CH_3)_3$, a variety of organo aluminum halides are formed. In the presence of NaCl for example, these organo aluminum halides would exist as sodium salts such as $Na[Al(CH_3)_2Cl_2]$, $Na[Al(CH_3)Cl_3]$ and the like. As is common with such inorganic species, the formulae are idealized and variety of more complex salts is always a possibility. In the method described above wherein a trialkyl aluminum is added to a freshly prepared tetrahalo gallate salt, such salts are expected, the distribution of which is determined to a large part by the relative amount of trialkyl aluminum to gallium salts. For example, a large excess of trimethyl aluminum would lead to large amounts of $Na[Al(CH_3)_3Cl]$, whereas larger amounts of $Na[Al(CH_3)Cl_3]$ is expected when the amount of trimethyl aluminum is kept to a minimum.

It has been found these salts, or similar salts, can be used as solvents for the transalkylation reaction between metal halides and alkyl metals. Many of these salts are molten at acceptably low temperatures and provide a fluid, non-volatile, ionic liquid medium for the reaction allowing for greater ease in mixing, shorter reaction times and greater flexibility in reactants while avoiding the possible contamination of the product by organic solvents and byproducts, especially as the solvent can be an intermediate that is already believed to be encountered during the reaction.

SUMMARY OF THE INVENTION

A method is provided for the preparation of trialkyl gallium and indium compounds by the addition of trialkyl aluminum to a mixture comprising gallium trihalide or indium trihalide and a halide salt of Li, Na, K or Cs in an ionic liquid. The desired trialkyl gallium or indium compound is isolated from the reaction mixture by distillation. In the reaction, at least two of the alkyl groups from the trialkyl aluminum are transferred to gallium or indium and the product is obtained in excellent purity in high yield. Given the need for ultra high purity organometallic compounds for many high value metal-containing films, the reaction is typically carried out in the absence of organic solvents.

A large number of ionic liquids are known from which a solvent for the present method can be chosen, but in many embodiments advantages may be realized by selecting a molten salt, or a mixture of salts, comprising the formula $M[AlR_nX_{(4-n)}]$ where M is Li, Na, K or Cs, X is a halide, R is an alkyl group and n is 1-3. Such salts generally melt at temperatures of 75° C. or higher so that heating to provide a fluid mixture is required. In many embodiments, the molten salts are themselves the byproduct of a reaction that also generates the desired trialkyl gallium and indium compounds, the salts being the residue remaining after the trialkyl gallium or indium compounds are separated from the reaction mixture.

As there is often a question as to the exact structure of an oganometallic compound or a metal halide compound, especially in a mixture of more than one such compound, the terms herein related to metal halide species such as aluminum, gallium and indium halide species, relate to stoichiometry only and does not necessarily imply a particular structure.

DESCRIPTION OF THE INVENTION

In one general embodiment of the invention, trialkyl metal compounds, for example, compounds of the formula $GaR_3$ or $InR_3$ are efficiently prepared in high yield by a method comprising:

a) adding $GaX_3$ or $InX_3$ and monovalent salt MX to an ionic liquid comprising one or more than one molten salt of the formula $M[AlR_nX_{(4-n)}]$ at a temperature between 75 and 160° C. to form a mixture of salts;

b) adding from 0.9 to 2.0, for example, 1.0 to 1.7, for example, 1.1 to 1.6 molar equivalents based on $GaX_3$ or $InX_3$ of $AlR_3$ to the mixture of salts formed in a), to form a reaction mixture; and c) distilling $GaR_3$ or $InR_3$ from the reaction mixture;

wherein each M is independently Li, Na, K or Cs, for example, Li, Na or K;

each X is independently F, Cl, Br or I, for example Cl or Br;

R is $C_{1-6}$ alkyl, for example $C_{1-4}$ alkyl; and n is 1-3.

Typically the amount of MX added is typically 0.9 to 2.0, for example, 1.0 to 1.7, for example, 1.1 to 1.6 molar equivalents based on the amount of added $GaX_3$ or $InX_3$.

To obtain even higher purity, additional distillations of the product can be performed, including distillation from a fluoride salt such as LiF, NaF etc, as is known in the art.

R, for example, is a $C_{1-4}$ alkyl, such as methyl, ethyl, propyl, isopropyl, butyl, sec-butyl, iso butyl and the like. In certain embodiments R is methyl or ethyl, for example, methyl.

There is no requirement that each X in the above method is the same halide. In many cases it is convenient to use a single halide in the reaction, e.g., gallium trichloride and sodium chloride can be added to molten $M[AlR_nCl_{(4-n)}]$, although it may be useful in certain cases to use mixed halides, for example, more than one gallium trihalide, such as trichloro gallium and tribromo gallium, or more than one mono or divalent metal halide for example, a mixture of sodium chloride and sodium iodide.

Often, each M is the same, each X is the same and each R is the same.

In certain embodiments X is Cl or Br and R is $C_{1-4}$ alkyl; for example X is Cl or Br and R is methyl or ethyl, often methyl.

While n can be a number from 1 to 3, it is often 1 or 2 and typically 1, however, it is common for a mixture of salts of the formula $M[AlR_nX_{(4-n)}]$ to be present as part of the ionic liquid solvent wherein n is any number from 1 to 3. In many embodiments the predominate compound of the ionic liquid solvent has an idealized formula $M[AlR_nX_{(4-n)}]$ wherein n is 1.

Given the availability of inexpensive sources of MX salts, it can be added in amounts higher than listed above, however excellent results are achieved when the amount of MX used is roughly the same amount on a molar basis as the amount of $AlR_3$ which is added. The reaction also will proceed well if $AlR_3$ is added in amounts higher than listed above, however this is not recommended given the high costs which would be encountered.

In the reaction, it is expected that at least two of the alkyl groups on the trialkyl aluminum are transferred to gallium or indium, and a molar ratio of approximately 1.5:1.0 of $AlR_3$ to $GaX_3$ or $InX_3$ provides excellent yields. Transfer of all three alkyl groups from aluminum to gallium or indium is also possible, but often requires higher reaction temperatures or longer reaction times. Therefore, when transferring more than two alkyl groups from aluminum, the reaction can be run with the addition of as little as approximately one molar equivalent of $AlR_3$ relative to $GaX_3$ or $InX_3$, or, e.g., as little as 1.1, 1.2, 1.3 or 1.4 equivalents. On the other hand, shorter reaction times and/or lower temperatures can be used when transfer of two alkyl groups from aluminum is planned, thus up to 1.6 molar equivalents of $AlR_3$ are often added, and to ensure complete conversion of gallium or indium trihalide in shorter reaction times, up to 1.7, 1.8 or 1.9 molar equivalents can be added. Use of more than 2 equivalents of $AlR_3$ is not typically necessary and adds to the cost.

The temperature of the reaction is not critical and is chosen to assure fluidity of the reaction mixtures to assure efficient stirring and good heat transfer. For example, heating at the melting point of the molten salt is often sufficient, although good conversion may require a period of mixing at higher temperatures. For example, in one embodiment the method comprises a) adding $GaX_3$ or $InX_3$ and monovalent salt MX to a molten salt of the formula $M[AlR_nX_{(4-n)}]$, at a temperature of from 100 to 130° C., for example, from about 110 to 125° C.; followed by b) adding from 0.9 to 2.0, for example, 1.0 to 1.7, for example, 1.1 to 1.6 molar equivalents based on $GaX_3$ or $InX_3$ of $AlR_3$ to the mixture of salts formed in a), to form a reaction mixture and then heating the reaction mixture at a temperature of from 120 and 160° C., for example from about 135 to about 150° C. to complete the reaction; and c) distilling $GaR_3$ or $InR_3$ from the reaction mixture.

While not wanting to be bound by theory, it is expected that a variety of inorganic species are generated during the course of the overall reaction, for example, a tetrahalo gallate or indium salt may be prepared in situ by reaction of the trihalide with MX, perhaps as an equilibrium mixture with the gallium or indium trihalide, MX and other possible arrangements of the added elements. As there is often a question as to the exact structure of an oganometallic compound or a metal halide compound, especially in a mixture of more than one such compound, the terms herein related to metal halide species such as aluminum, gallium and indium halide species, refer to relative stoichiometry only and do not necessarily imply a particular structure. Of course, once reaction with trialkyl aluminum begins, mixtures of various intermediate alkyl-metal compounds will also be present leading to the formation of the trialkyl gallium or indium compounds.

A large number of ionic liquids are known from which a solvent for the present method can be chosen. One advantage of selecting a compound of $M[AlR_nX_{(4-n)}]$ as solvent, especially when the R group of the solvent is the same as that of the trialkyl aluminum, is that it introduces no materials which are not encountered as part of the desired overall chemical conversion. That is, no unwanted side reaction with the solvent will take place which may contaminate the final product.

The ionic liquid solvent comprising one or more salts of formula $M[AlR_nX_{(4-n)}]$ can itself be obtained from a reaction which also yields trialkyl gallium or indium compounds by reacting trialkyl aluminum and trihalo gallium or indium in the presence of a salt MX, or reaction between trialkyl aluminum and a tetrahalo gallium or indium salt, preferably in the absence of an organic solvent. For example, sodium chloride and molten gallium trichloride can be mixed at temperatures sufficient to melt gallium trichloride, e.g., about 80° C. to obtain a sodium tetrachloro gallate product mixture. Trialkyl aluminum is then added directly to this mixture, optionally with additional heating, for example up to 140° C. or 150° C. Distillation removes the trialkyl gallium leaving the mixed salts in the reaction vessel, which may be removed or to which additional reactants is added directly. The amount of salts left in the reaction vessel, and their composition can be determined by the stoicheometry, for example, addition of 1.5 equivalents of trialkyl aluminum and 1.5 equivalents of sodium chloride to 1 equivalent of gallium trichloride will generate mainly $Na[AlRX_3]$.

During the course of the reaction, which can be run batch wise, continuously or semi-continuously, more aluminum halide salts, including $M[AlR_nX_{(4-n)}]$ salts, are generated. Thus, as the reaction progresses, additional solvent is generated. In one embodiment, upon formation of large amounts of aluminate salt, for example in a continuous or semi continuous process, excess aluminate salt is removed from the reactor after isolation of the desired product, for example through a bottom release valve, and then steps a) through c) are run using the mixture of salts left in the reactor as solvent. Typically, prior to removing the excess salt, a vacuum may be applied to the reaction mixture to remove any volatile products entrained in the solvent. The excess salt may be disposed of or recycled, for example, as solvent for the present method or other reactions.

One example of a continuous process of the instant method comprises preparing a mixture of sodium chloride in molten gallium trichloride at about 80 to 125° C. and adding thereto trimethyl aluminum with vigorous agitation and heating to about 140° C. to form trimethyl gallium and $Na[Al(CH_3)Cl_3]$. The relative amounts of each component, $GaCl_3$, NaCl and $Al(CH_3)_3$ can conveniently be selected from those defined above. Trimethyl gallium is isolated by distillation leaving behind in the reaction vessel a quantity of $Na[Al(CH_3)Cl_3]$, mp 120° C., or a mixture containing $Na[Al(CH_3)Cl_3]$. $GaCl_3$ and NaCl are then added to the reaction vessel containing the molten salt heated at about 120° C. and then $Al(CH_3)_3$ is added. The relative amounts of each component are defined above and the total amount of reactants is determined primarily by the amount which can be adequately mixed in the amount of molten salt generated in the original trimethyl gallium forming reaction. The mixture is then heated at 140° C. to complete the reaction, with the trimethyl gallium again isolated by distillation, leaving behind a larger quantity of molten salt to which additional $GaCl_3$ and NaCl are added followed by $Al(CH_3)_3$. The sequence, that is each iteration of steps a), b) and c), is repeated until the amount of salt remaining after distillation of trimethyl gallium is considered excessive for the size of the reaction vessel.

At this point, a vacuum may be applied to aid in the removal of any additional volatiles after which an amount of the excess solvent salt is removed. $GaCl_3$ and NaCl can then be added to the reaction vessel containing the residual molten salt heated at about 120 C and $Al(CH_3)_3$ is then added and the sequence continues. Following this method, using a molar ratio of $GaCl_3$:NaCl:$Al(CH_3)_3$ of approximately 1:1.5:1.5 for each reaction sequence and combining the trimethyl gallium distilled after each iteration, 100 grams of $Ga(CH_3)_3$ was prepared in excellent purity. A kilogram quantity was also produced upon scale up to a larger reaction vessel.

The molten solvent salt removed can be used as solvent for other reactions, for example, the preparation of trimethyl indium from $InCl_3$ according to the present invention.

The method as described using a molten salt as solvent allows for good mixing throughout the reaction process and good heat transfer thus improving safety. By choosing the appropriate salt as solvent, side reactions with organic solvents etc are prevented and high conversion and purity is achieved. Further, following a variant of the "continuous process" above allows one to prepare a larger quantity of trialkyl metal compound without cleaning out the reaction vessel between batches.

Just as the exact temperature of the reaction will depend on what is needed for good mixing, the exact composition and amount of ionic liquid solvent will also vary depending on the reaction design. While there are certain benefits in having each group M and X be the same, there is no requirement that this be so. When various M and X groups are introduced into the reaction, the make up of the salts forming the ioninc liquid solvent will also change as the reaction proceeds. Thus, the temperature needed for the process may vary as the make up of the solvent changes. Also, the amount of ionic liquid needed to provide for adequate mixing of the reaction mixture may vary depending on the reaction specifics. Generally, during the operation of the process, the amount of the at least one molten salt of the formula $M[AlR_nX_{(4-n)}]$, will be equal to or exceed, on a molar basis, the total amount of trihalo and tetrahalo gallium or indium compound present in the reaction mixture, as determined by the amount of gallium or indium reactant added minus the amount product removed. Of course as the reaction to form the trialkyl gallium or indium proceeds, additional salts of the formula $M[AlR_nX_{(4-n)}]$ are formed, thus increasing the amount of the molten salt solvent, so that once begun, the limits of how much trihalo gallium or indium, and by extension $AlR_3$, added to the reaction vessel before the removal of excess solvent depend largely on the size of the vessel.

By following the general procedure of the above continuous process and obvious variants thereof, including batch processes, the trialkyl gallium and indium compounds of the invention can be prepared.

Because many desirable trialkyl gallium and trialkyl indium compounds are relatively volatile, they are easily isolated from the reaction mixture by simple distillation. However, some desirable compounds are less volatile and may require reduced pressure, e.g., by applying a vacuum during distillation. Solid compounds such as trimethyl indium can be isolatted by sublimation, which is considered herein to be a form of distillation wherein a solid rather than a liquid is collected.

While the reaction used in the present method potentially involves a number of chemical transformations of the initial aluminum and gallium reactants, the actual process steps are quite straight forward. The standard precautions against introducing water etc to the reaction or generating an unwanted excessive exotherm must be observed, but the process is simple, no unusual processing steps or conditions are employed and standard equipment can be readily employed.

EXAMPLES

Example 1

Preparation of Ionic Liquid Solvent and TMG (Trimethyl Gallium)

To a reaction vessel equipped for distillation is added 209 g (1.19 mol) $GaCl_3$ and 107 g (1.83 mol) NaCl. The mixture is heated to 125° C. with stirring and 134 g (1.86 mol) of TMA (trimethyl aluminum) are added at a rate which maintains a reaction temperature in the range of 120 to 145° C. while ensuring that the head temperature of the simultaneous distillation of trimethyl gallium does not exceed 60° C. Several solid, salt like intermediates are formed during the reaction and difficulties in stirring and temperature control are encountered. After addition of TMA is completed the temperature in the reaction vessel is maintained at approximately 140 to 145° C. and the distillation of the TMG product is continued until collection stops, at which point a vacuum at 30 mbar is applied in order to remove all remaining volatiles. A 97% yield of TMG based on $GaCl_3$ is obtained.

The residue from Example 1 which remains in the reaction vessel after distillation is complete comprises the salt $Na[Al(CH_3)Cl_3]$.

Example 2

Preparation of TMG in of Ionic Liquid Solvent

The salt residue from Example 1 is heated to liquefaction at a temperature of 120 to 135° C. The molten salt is stirred and 174 g (1 mol) $GaCl_3$ and 97 g (1.66 mol) NaCl are added while maintaining a temperature of 120 to 135° C. To this solution 111 g (1.54 mol) of TMA are added at a rate which maintains a reaction temperature in the range of 120 to 145° C. while ensuring that the head temperature of the simultaneous distillation of trimethyl gallium does not exceed 60° C. While the same solid, salt like intermediates encountered in Example 1 are undoubtedly formed, no difficulties in stirring the fluid reaction mass occurs. After addition of TMA is completed the temperature in the reaction vessel is maintained at approximately 140 to 145° C. and the distillation of the TMG product is continued until collection stops, at which point a vacuum at 30 mbar is applied in order to remove all remaining volatiles. A 98% yield of TMG based on $GaCl_3$ is obtained.

Example 3

Preparation TMG in Molten Salts

The residue in the reaction vessel from Example 2 is heated to 120 to 135° C. and the procedure of Example 2 is repeated using 173 g (0.98 mol) GaCl$_3$, 89 g (1.52 mol) NaCl and 110 g (1.53 mol) of TMA. Yield of TMG based on GaCl$_3$ is 96%: Analysis of this crude material: Al: 0.54%; Cl: 0.62%

What is claimed:

1. A method for preparing trialkyl metal compounds of the formula GaR$_3$ or InR$_3$ comprising:
   a) adding GaX$_3$ or InX$_3$ and monovalent salt MX to an ionic liquid comprising one or more than one molten salt of the formula M[AlR$_n$X$_{(4-n)}$] at a temperature of from 75 to 160° C. to form a mixture of salts;
   b) adding from 0.9 to 2.0 molar equivalents of AlR$_3$, based on moles of GaX$_3$ or InX$_3$, to the mixture of salts formed in a) to form a reaction mixture, and
   c) distilling GaR$_3$ or InR$_3$ from the reaction mixture;
   wherein each M is independently Li, Na, K or Cs; each X is independently is F, Cl, Br or I; R is C$_{1-6}$ alkyl; n is a number of from 1 to 3; and wherein the amount of MX added is 1.0 to 2.0 molar equivalents of the amount of added GaX$_3$ or InX$_3$.

2. The method according to claim 1 wherein R is C$_{1-4}$ alkyl.

3. The method according to claim 1 wherein R is methyl or ethyl.

4. The method according to claim 1 wherein M is Li, Na or K.

5. The method according to claim 1 wherein 1.0 to 1.7 molar equivalents of AlR$_3$, based on moles of GaX$_3$ or InX$_3$ is added in b).

6. The method according to claim 5 wherein 1.2 to 1.6 molar equivalents of AlR$_3$ based on moles of GaX$_3$ or InX$_3$ is added in b).

7. The method according to claim 1 further comprising performing additional sequences of a), b) and c), wherein the compound of formula GaR$_3$ or InR$_3$ isolated during each sequence is combined and optionally further purified.

8. The method according to claim 1 wherein isolated GaR$_3$ or InR$_3$ is purified by distillation from a mixture containing a fluoride salt.

9. The method according to claim 5 wherein 1.0 to 1.7 molar equivalents of MX based on moles of GaX$_3$ or InX$_3$ is added in a).

10. The method according to claim 6 wherein 1.2 to 1.6 molar equivalents of MX, based on moles of GaX$_3$ or InX$_3$ is added in a).

11. The method according to claim 1 wherein M is Li, Na or K; X is Cl or Br; and R is methyl or ethyl and each M and each X is the same.

12. The method according to claim 1 wherein vacuum is applied to aid in distillation.

13. The method according to claim 1 wherein the ionic liquid solvent comprising one or more salts of formula M[AlR$_n$X$_{(4-n)}$] is first obtained by reacting trialkyl aluminum and trihalo gallium or indium in the presence of a salt MX, or reaction between trialkyl aluminum and a tetrahalo gallium or indium salt in the absence of an organic solvent.

14. The method according to claim 1 wherein a compound of formula GaR$_3$ is prepared from a compound of formula GaX$_3$.

15. The method according to claim 14 wherein isolated GaR$_3$ is purified by distillation from a mixture containing a fluoride salt.

16. The method according to claim 5 wherein a compound of formula GaR$_3$ is prepared from a compound of formula GaX$_3$.

17. The method according to claim 7 wherein a compound of formula GaR$_3$ is prepared from a compound of formula GaX$_3$.

18. The method according to claim 1 wherein a compound of formula InR$_3$ is prepared from a compound of formula InX$_3$.

19. The method according to claim 5 wherein a compound of formula InR$_3$ is prepared from a compound of formula InX$_3$.

20. The method according to claim 7 wherein a compound of formula InR$_3$ is prepared from a compound of formula InX$_3$.

* * * * *